(12) United States Patent  (10) Patent No.: US 8,855,735 B2
Li                          (45) Date of Patent:     Oct. 7, 2014

(54) MEDICAL SENSOR USING PHOTONIC CRYSTAL LED

(75) Inventor: Youzhi Li, Longmont, CO (US)

(73) Assignee: Covidien LP, Mansfield, MA (US)

( * ) Notice: Subject to any disclaimer, the term of this patent is extended or adjusted under 35 U.S.C. 154(b) by 626 days.

(21) Appl. No.: 13/034,454

(22) Filed: Feb. 24, 2011

(65) Prior Publication Data

US 2012/0220841 A1    Aug. 30, 2012

(51) Int. Cl.
*A61B 5/1455* (2006.01)
*G01J 3/10* (2006.01)
*G01J 3/42* (2006.01)
*G01N 21/31* (2006.01)
*G01N 21/35* (2014.01)

(52) U.S. Cl.
CPC ........... *G01J 3/10* (2013.01); *A61B 2560/0209* (2013.01); *A61B 5/14552* (2013.01); *G01N 2021/3144* (2013.01); *G01N 2021/3181* (2013.01); *H01L 2933/0083* (2013.01); *G01N 21/359* (2013.01); *G01J 3/42* (2013.01); *G01N 21/3151* (2013.01)
USPC ............................ 600/323; 600/310; 600/322

(58) Field of Classification Search
USPC ................................. 600/309–344
See application file for complete search history.

(56) References Cited

U.S. PATENT DOCUMENTS

| 6,356,774 B1 * | 3/2002 | Bernstein et al. ............. 600/323 |
| 6,611,320 B1 * | 8/2003 | Lindberg et al. ................ 356/40 |
| 7,162,288 B2 | 1/2007 | Nordstrom et al. |
| 7,171,251 B2 | 1/2007 | Sarussi et al. |
| 7,277,741 B2 | 10/2007 | Debreczeny et al. |
| 7,460,248 B2 | 12/2008 | Kurtz et al. |
| 7,532,919 B2 | 5/2009 | Soyemi et al. |
| 2005/0084202 A1 | 4/2005 | Smith et al. |
| 2006/0224053 A1 | 10/2006 | Black et al. |
| 2006/0253007 A1 | 11/2006 | Cheng et al. |
| 2007/0093702 A1 | 4/2007 | Yu et al. |
| 2007/0149871 A1 | 6/2007 | Sarussi et al. |
| 2007/0293746 A1 | 12/2007 | Sarussi et al. |
| 2008/0076988 A1 | 3/2008 | Sarussi et al. |
| 2008/0076990 A1 | 3/2008 | Sarussi et al. |
| 2008/0221462 A1 * | 9/2008 | Baker ........................... 600/485 |

FOREIGN PATENT DOCUMENTS

| DE | 3516338 | 11/1986 |
| DE | 3703458 | 8/1988 |
| DE | 19632361 | 2/1997 |
| EP | 0127947 | 12/1984 |

(Continued)

OTHER PUBLICATIONS

Barton, D., et al., "Photonic crystals improve LED efficiency," SPIE the International Society for Optical Engineering, SPIE Newsroom, 10.1117/2.1200603.0160; 2 pages (2006).

(Continued)

*Primary Examiner* — Eric Winakur
*Assistant Examiner* — Marjan Fardanesh
(74) *Attorney, Agent, or Firm* — Fletcher Yoder PC

(57) ABSTRACT

Systems and methods are provided for spectrophometric measurement of a physiological property of a patient. For example, an embodiment of a patient monitoring system may include a monitor operatively coupled to a spectrophotometric sensor, which may include an emitter configured to transmit light into tissue of the patient and a detector configured to receive the light from the tissue. The emitter may use a photonic crystal light emitting diode to generate the light.

21 Claims, 6 Drawing Sheets

(56) References Cited

FOREIGN PATENT DOCUMENTS

| EP | 0204259 | 12/1986 |
|---|---|---|
| EP | 0531631 | 3/1993 |
| FR | 2685865 | 7/1993 |
| JP | 6014906 | 1/1994 |
| WO | WO9309711 | 5/1993 |
| WO | WO9502358 | 1/1995 |
| WO | WO9736536 | 10/1997 |
| WO | WO2007051066 | 5/2007 |

OTHER PUBLICATIONS

Weisbuch, C., et al., "The Physics of Photonic Crystals and LEDs," The 23rd General Conference of the Condensed Matter Division of the European Physical Society under the auspices of Polish Physical Society and Honorary Patronage of the Rector of the University of Warsaw—Prof. D.SC. Katarzyna Chalasinska-Macukow; http://dsid.ipj.gov.pl/files/CMD23/Claude-Weisbuch_CMD23.pdf; 72 pages (Aug. 30-Sep. 3, 2010).
Rahman, F., "Photonic Crystal LEDs," OPN, pp. 24-29 (Jun. 2009).
"Cree's High-Power White LED Delivers 121 lm/W;" U.S. Department of Energy—Energy Efficiency and Renewable Energy, Solid-State Lighting, http://www1.eere.energy.gov/buildings/ssl/printable_version/cree_white_led.html, 1 page (last viewed Dec. 7, 2010).
"Photonic-crystal LED reaches 73% light-extraction efficiency," LEDs Magazine, http://www.ledsmagazine.com/news/6/3/15; 1 page (Mar. 20, 2009).
Rahman, F., et al., "Photonic Crystal Enable Ultrabright LEDs," Photonics.com, http://www.photonics.com/ArticlePrint.aspx?AID=30141, 4 pages (Jul. 1, 2007).
"Photonics and nano particles brighten LEDs," LuxtalTek Corporation, http://www.luxtaltek.com/news/news_content_03.html, 2 pages (last viewed Apr. 2, 2010).
Faisst, K., et al.; "Intrapartum Reflectance Pulse Oximetry: Effects of Sensor Location and Fixation Duration on Oxygen Saturation Readings," *Journal of Clinical Monitoring*, vol. 13, pp. 299-302 (1997).
Izumi, A., et al.; "Accuracy and Utility of a New Reflectance Pulse Oximeter for Fetal Monitoring During Labor," *Journal of Clinical Monitoring*, vol. 13, pp. 103-108 (1997).
"Smaller Product, Tighter Tolerances Pose Dispensing Challenges for Medical Device Manufacturer," *Adhesives Age*, pp. 40-41 (Oct. 1997).
Crilly, P., et al.; "An Integrated Pulse Oximeter System for Telemedicine Applications," *IEEE Instrumentation and Measurement Technology Conference*, Ottawa, Canada; May 19-21, 1997; pp. 102-104.
Dekock, M.; "Pulse Oximetry Probe Adhesive Disks: a Potential for Infant Aspiration," *Anesthesiology*, vol. 89, pp. 1603-1604 (1998).
Rhee, S., et al.; "The Ring Sensor: a New Ambulatory Wearable Sensor for Twenty-Four Hour Patient Monitoring," *Proceedings of the 20th annual International Conference of the IEEE Engineering in Medicine and Biology Society*, 1998, vol. 20, No. 4, pp. 1906-1919.
Yang, B., et al.; "A Twenty-Four Hour Tele-Nursing System Using a Ring Sensor," *Proceedings of the 1998 IEEE International Conference on Robotics & Automation*, Leaven, Belgium, May 1998; pp. 387-392.
Lutter, N., et al.; "Comparison of Different Evaluation Methods for a Multi-wavelength Pulse Oximeter," *Biomedizinische Technik*, vol. 43, (1998).
Ferrell, T.L., et al.; "Medical Telesensors," *SPIE*, vol. 3253, pp. 193-198 (1998).
Ikeda, K., et al.; "Improvement of Photo-Electric Plethysmograph Applying Newly Developed Opto-Electronic Devices," *IEEE Tencon*, pp. 1109-1112 (1999).
Yang, B., et al.; "Development of the ring sensor for healthcare automation," *Robotics and Autonomous Systems*, vol. 30, pp. 273-281 (2000).
Rhee, S., et al.; "Artifact-Resistant, Power-Efficient Design of Finger-Ring Plethysmographic Sensor—Part I: Design and Analysis," *Proceedings of the 22nd Annual EMBS International Conference*, Chicago, Illinois; Jul. 23-28, 2000; pp. 2792-2795.
Rhee, S., et al.; "Artifact-Resistant, Power-Efficient Design of Finger-Ring Plethysmographic Sensor—Part II: Prototyping and Benchmarking," *Proceedings of the 22nd Annual EMBS International Conference*, Chicago, Illinois; Jul. 23-28, 2000; pp. 2796.
Schulz, C.; "Design of a Pulse Oximetry Sensor Housing Assembly," California State University Master's Thesis, *UMI Dissertation Services*, UMI No. 1401306, (May 2000) 63 pages.
Yokota, N., et al.; "Pilot Model of a Reflectance-Type Pulse Oximeter for Pre-hospital Evaluation," *Journal of the Japanese Society of Emergency Medicine*, Kanto Region, vol. 21, pp. 26-27 (2000) (Article in Japanese—contains English summary.
Cubeddu, R., et al.; "Portable 8-channel time-resolved optical imager for functional studies of biological tissues," *Photon Migration, Optical Coherence Tomography, and Microscopy, Proceedings of SPIE*, vol. 4431, pp. 260-265 (2001).
Gisiger, P.A., et al.; "OxiCarbo®, a single sensor for the non-invasive measurement of arterial oxygen saturation and $CO_2$ partial pressure at the ear lobe," *Sensor and Actuators*, vol. B-76, pp. 527-530 (2001).
Rhee, S., et al.; "Artifact-Resistant, Power-Efficient Design of Finger-Ring Plethysmographic Sensor," *IEEE Transactions on Biomedical Engineering*, vol. 48, No. 7, pp. 795-805 (Jul. 2001).
Lopez-Silva, S., et al.; "NIR transmittance pulse oximetry system with laser diodes," *Clinical Diagnostic Systems, Proceedings of SPIE*, vol. 4255, pp. 80-87 (2001).
Maletras, F., et al.; "Construction and calibration of a new design of Fiber Optic Respiratory Plethysmograph (FORP)," *Optomechanical Design and Engineering, Proceedings of SPIE*, vol. 4444, pp. 285-293 (2001).
Earthrowl-Gould, T., et al.; "Chest and abdominal surface motion measurement for continuous monitoring of respiratory function," *Proc. Instn Mech Engrs*, V215, Part H; pp. 515-520 (2001).
Liu, Y., et al.; "Sensor design of new type reflectance pulse oximetry," *Optics in Health Care and Biomedical Optics: Diagnostics and Treatment, Proceedings of SPIE*, vol. 4916, pp. 98-102 (2002).
Irie, A., et al.; "Respiration Monitors—Pulse Oximeters," *Neonatal Care*, vol. 15, No. 12, pp. 78-83 (2002) (Article in Japanese—contains English summary of article).
Shaltis, P., et al.; "Implementation and Validation of a Power-Efficient, High-Speed Modulation Design for Wireless Oxygen Saturation Measurement Systems," *IEEE*, pp. 193-194 (2002).
Warren, S., et al.; "Wearable Sensors and Component-Based Design for Home Health Care," *Proceedings of the Second Joint EMBS/BMES Conference*, Houston, Texas; Oct. 23-26, 2002; pp. 1871-1872.
Lopez-Silva, S., et al.; "Near-infrared transmittance pulse oximetry with laser diodes," *Journal of Biomedical Optics*, vol. 8, No. 3, pp. 525-533 (Jul. 2003).
Mendelson, Y., et al.; "Measurement Site and Photodetector Size Considerations in Optimizing Power Consumption of a Wearable Reflectance Pulse Oximeter," *Proceedings of the 25th Annual International conference of the IEEE EMBS*, Cancun, Mexico, Sep. 17-21, 2003.
Matsui, A., et al.; "Pulse Oximeter," *Neonatal Care*, vol. 16, No. 3, pp. 38-45 (2003) (Article in Japanese—contains English summary of article).
Nakagawa, M., et al.; "Oxygen Saturation Monitor," *Neonatal Monitoring*, vol. 26, No. 5, pp. 536-539 (2003) (Article in Japanese—contains English summary of article).
Pujary, C., et al.; "Photodetector Size Considerations in the Design of a Noninvasive Reflectance Pulse Oximeter for Telemedicine Applications," *IEEE*, pp. 148-149 (2003).
Lopez-Silva, S., et al.; "Transmittance Photoplethysmography and Pulse Oximetry With Near Infrared Laser Diodes," *IMTC 2004—Instrumentation and Measurement Technology Conference*, Como, Italy, May 18-20, 2004; pp. 718-723.
Urquhart, C., et al.; "Ear probe pulse oximeters and neonates," *Anaesthesia*, vol. 60, p. 294 (2005).
Odagiri, Y.; "Pulse Wave Measuring Device," *Micromechatronics*, vol. 42, No. 3, pp. 6-11 (undated) (Article in Japanese—contains English summary of article).
Bentley, D. et al.; "Measure Pressure with Thin Film," Paper Film & Foil Converter; May 1, 2003 (4 pages).
http://www.cfw.com.my/fujifilm.html (4 pages).

\* cited by examiner

MEDICAL SENSOR USING PHOTONIC CRYSTAL LED

BACKGROUND

The present disclosure relates generally to medical sensors and, more particularly, to sensors used for sensing physiological parameters of a patient.

This section is intended to introduce the reader to various aspects of art that may be related to various aspects of the present disclosure, which are described and/or claimed below. This discussion is believed to be helpful in providing the reader with background information to facilitate a better understanding of the various aspects of the present disclosure. Accordingly, it should be understood that these statements are to be read in this light, and not as admissions of prior art.

Many types of medical sensors, such as optical sensors, are used to measure physiological characteristics of a patient. Typically, an optical sensor provides emitted light, which is then scattered through a portion of a tissue of a patient and detected. Various characteristics of a patient can be determined from analyzing such light, such as oxygen saturation, pulse rate, tissue bilirubin, and so forth.

Pulse oximetry is typically used to measure various blood flow characteristics including, but not limited to, the blood-oxygen saturation of hemoglobin in arterial blood, the volume of individual blood pulsations supplying the tissue, and the rate of blood pulsations corresponding to each heartbeat of a patient. Measurement of these characteristics has been accomplished by use of a non-invasive sensor, which scatters light through a portion of the tissue of the patient where blood perfuses the tissue, and photoelectrically senses the absorption of light in such tissue. The amount of light absorbed and/or scattered is then used to calculate the amount of blood constituent being measured.

The light transmitted through the tissue is selected to be of one or more wavelengths that are absorbed by the blood in an amount representative of the amount of the blood constituent present in the blood. The amount of transmitted light scattered through and/or absorbed by the tissue will vary in accordance with the changing amount of blood constituent in the tissue. For measuring blood oxygen level, such sensors have typically been provided with a light source that is adapted to generate light of at least two different wavelengths, in accordance with known techniques for measuring blood oxygen saturation.

Known non-invasive sensors include devices that use conventional light emitting diodes (LEDs) as light sources. However, such LEDs may have low emission efficiencies, which may result in high power consumption. Increased power consumption may lead to increased heat generation. In addition, the spatial profiles of such LEDs may be difficult to control, which may increase the complexity of sensors incorporating these LEDs.

BRIEF DESCRIPTION OF THE DRAWINGS

Advantages of the disclosed techniques may become apparent upon reading the following detailed description and upon reference to the drawings in which.

DETAILED DESCRIPTION OF SPECIFIC EMBODIMENTS

One or more specific embodiments of the present techniques will be described below. In an effort to provide a concise description of these embodiments, not all features of an actual implementation are described in the specification. It should be appreciated that in the development of any such actual implementation, as in any engineering or design project, numerous implementation-specific decisions must be made to achieve the developers' specific goals, such as compliance with system-related and business-related constraints, which may vary from one implementation to another. Moreover, it should be appreciated that such a development effort might be complex and time consuming, but would nevertheless be a routine undertaking of design, fabrication, and manufacture for those of ordinary skill having the benefit of this disclosure.

Sensors for pulse oximetry or other applications using spectrophotometry, such as hemometry and aquametry, may include the use of photonic crystal (PhC) light emitting diodes (LEDs). As described in detail below, PhC LEDs use etched photonic crystal lattices that may allow for increased surface brightness and an improved spatial emission profile compared to conventional LEDs. For example, PhC LEDs may provide the same level of brightness as conventional LEDs at a lower level of power because PhC LEDs may be more efficient that conventional LEDs. The reduced power consumption of PhC LEDs may also reduce the amount of heat produced by the PhC LEDs. Furthermore, the improved spatial emission profile of PhC LEDs enables additional components, such as lenses, ground glass, and so forth, used to control the spatial emission profile of conventional LEDs to be omitted. Thus, sensors that incorporate PhC LEDs may also use less power, generate less heat, and be less complicated and expensive than sensors using conventional LEDs. In certain embodiments, the operation of certain components of sensors using PhC LEDs, such as pulse signal servos, may be modified and/or simplified in response to the lower power consumption of PhC LEDs, for example.

Figure 1:
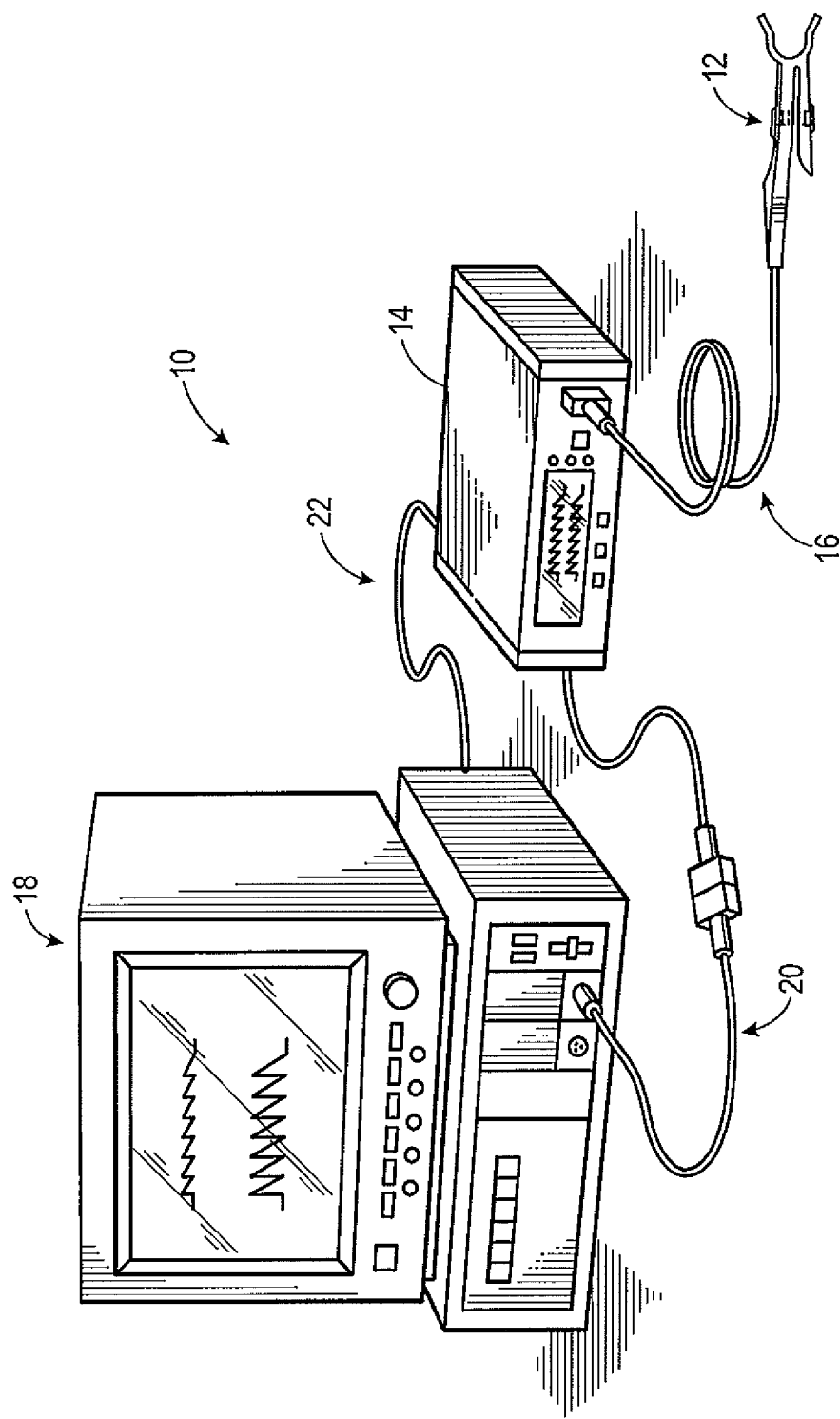
FIG. 1 illustrates an embodiment of a spectrophotometric system.

With the foregoing in mind, FIG. 1 depicts a spectrophotometric system 10, such as a pulse oximeter, hemometer, and/or aquameter. The sensor 12 may be coupled to the monitor 14 via sensor cable 16. As described in detail below, the sensor 12 may use one or more PhC LEDs. The spectrophotometric system 10 may be any suitable pulse oximeter, hemometer, and/or aquameter, such as those available from Nellcor Puritan Bennett, LLC. Furthermore, to upgrade conventional operation provided by the monitor 14 to provide additional functions, the monitor 14 may be coupled to a multi-parameter patient monitor 18 via a cable 20 connected to a sensor input port or via a cable 22 connected to a digital communication port, for example.

Figure 2:
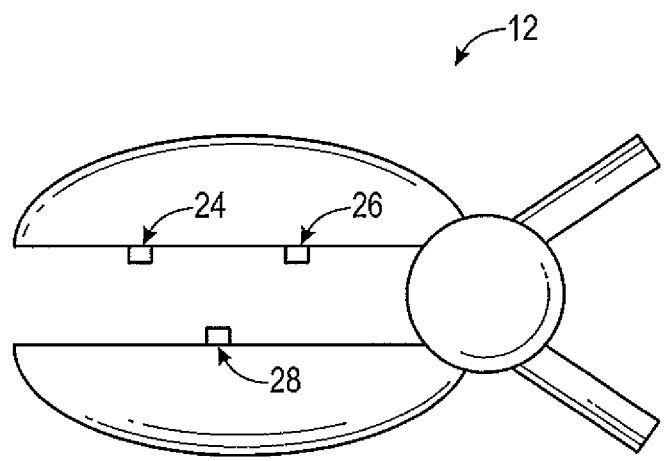
FIG. 2 illustrates an embodiment of a sensor having two photonic crystal (PhC) LEDs with a photodetector positioned to receive the PhC LED signals in a transmission mode of operation.
Figure 3:
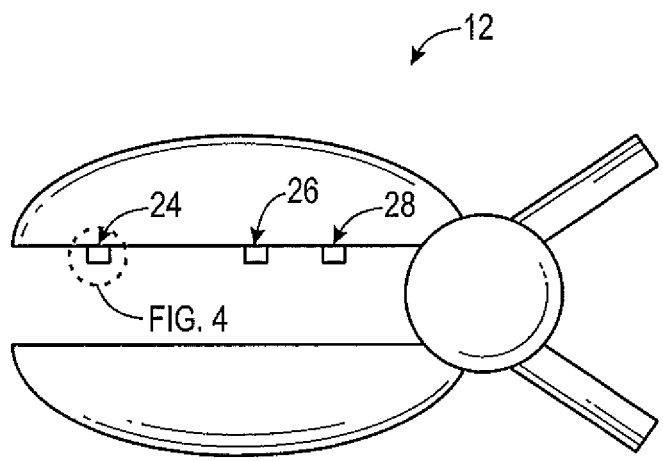
FIG. 3 illustrates an embodiment of a sensor having two PhC LEDs with a photodetector positioned to receive the PhC LED signals in a reflectance mode of operation.

In an embodiment, the sensor 12 may include two PhC LEDs emitting at different wavelength ranges, as depicted in more detail in FIGS. 2 and 3. For example, in a pulse oximetry embodiment, the two wavelength ranges may include a red wavelength at approximately 620-700 nm and an infrared wavelength at approximately 860-940 nm. A 660 nm emitter and a 900 nm emitter may respectively emit light within each of the two wavelength ranges. A 660 nm emitter emits a wavelength of light that has a relatively high reduced hemoglobin (Hb) absorption coefficient but a relatively low oxyhemoglobin ($HbO_2$) absorption coefficient. A 900 nm emitter emits a wavelength of light that has different absorption coefficients for Hb and $HbO_2$ from the light emitted by the 660 nm emitter. The absorption difference may be used to derive a more accurate peripheral oxygen saturation ($SpO_2$) measurement. For example, by analyzing the light emitted by the 660 nm emitter and by the 900 nm emitter, a more accurate measurement may be obtained in the high $SpO_2$ range (e.g., greater than 84%). It is to be understood that, in other embodiments, more emitters may be used and/or different wavelengths may be emitted. For example, in a regional oxygen saturation embodiment, the emitted wavelength ranges may include a far red wavelength at approximately 735 nm, and an infrared wavelength at approximately 808 nm.

With the foregoing discussion of various sensors 12 in mind, FIG. 2 illustrates a transmission type sensor 12 wherein light from a first PhC LED emitter 24 and light from a second PhC LED emitter 26 passes through one side of a vascularized tissue to reach a detector 28 on the other side of the tissue. FIG. 3 depicts a reflectance type sensor 12 wherein the first PhC LED emitter 24, the second PhC LED emitter 26, and the detector 28 are all positioned on the same side of the sensor 12 so that the emitted light is reflected through the vascularized tissue underneath the emitters back into the detector 28. As mentioned above, the sensor 12 may be a pulse oximetry sensor. Accordingly, the first and second emitters 24 and 26 may emit light at approximately 660 nm and 900 nm respectively. It should be noted that more or fewer emitters may be used, depending on the sensing capabilities included in the sensor 12. It should also be noted that the spacing of the first and second emitters 24 and 26 and the detector 28 of FIGS. 2 and 3 are for illustrative purposes and not to scale. Indeed, the same light path length for all emitter-detector pairs is usually preferred, and accordingly, the PhC LEDs 24 and 26 may be positioned in close proximity to each other.

Figure 4:
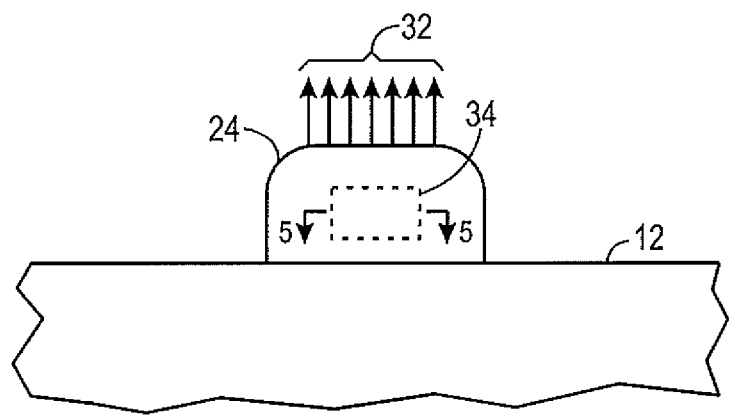
FIG. 4 illustrates a partial side elevational view of a PhC LED disposed on an embodiment of a sensor.

To illustrate how light may be emitted from the PhC LEDs 24 and 26, FIG. 4 is a drawing of the PhC LED emitter 24 disposed on the sensor 12. As discussed in detail below, the PhC LED emitter 24 has an improved spatial emission profile compared to that of conventional LEDs. As illustrated in FIG. 4, light rays 32 emitted from the PhC LED emitter 24 are nearly parallel or semi-collimated. Thus, the light rays 32 from the PhC LED emitter 24 may be directed to a specific location or tissue of the patient without the use of lenses, for example. Thus, the configuration of the sensor 12 may be simpler than sensors 12 using conventional LEDs. Further, the collimated nature of the lights rays 32 emitted from the PhC LED emitter 24 enables more light from the emitter 24 to be directed toward the tissue of the patient. Thus, the sensor 12 may use less power because more of the light rays 32 reach the targeted area of the patient. In other embodiments, the light rays 32 emitted from the PhC LED emitter 24 may not be entirely collimated, but the spatial emission profile of the PhC LED emitter 24 may still better than that of conventional LEDs.

Figure 5:
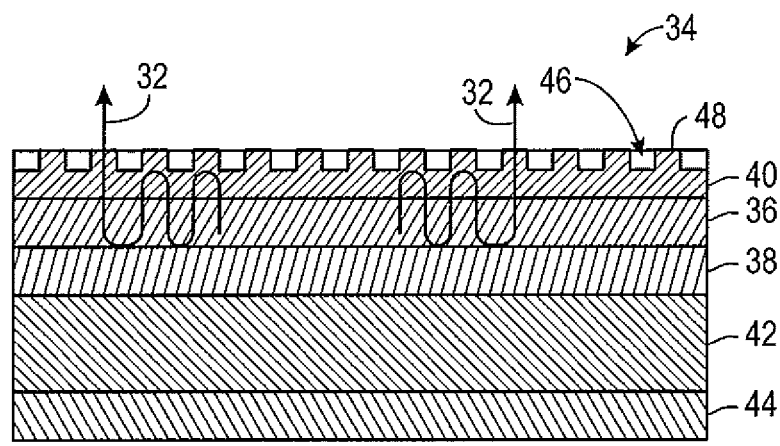
FIG. 5 illustrates a cross-sectional view of an embodiment of a PhC LED.

To illustrate the internal structure and operation of the PhC LED emitter 24, FIG. 5 is a cross sectional view of a portion 34 of the PhC LED emitter 24 along the line labeled 5-5 in FIG. 4. Light 32 is generated in a light emitting quantum well region 36. In other words, the quantum well region 36 is a potential well with only discrete energy values. The quantum well region 36 may include several layers of materials sandwiched together. For example, in certain embodiments, the quantum well region 36 may include gallium arsenide sandwiched between two layers of aluminum arsenide. In other embodiments, the quantum well region 36 may include gallium nitride. Located below the quantum well region 36 is an n-type contact 38, which produces an excess of negative (n-type) electron charge carriers. The n-type contact 38 may be made from a semiconductor in which dopant atoms are capable of providing extra conduction electrons to a host material. Located above the quantum well region 36 is a p-type contact 40, which produces an excess of free charge (p-type) carriers. The p-type contact 40 is doped, such that the number of free charge carriers, which are positive, is increased. Together, the quantum well region 36, the n-type contact 38, and the p-type contact 40 constitute a diode of the PhC LED emitter 24. The diode of the PhC LED emitter 24 is disposed on a sapphire substrate 42, which is transparent, thus enabling light to propagate through the sapphire substrate 42. Located below the sapphire substrate 42 is a reflective coating 44, which reflects any light that passes through the sapphire substrate 42. Thus, the reflective coating 44 may reflect any light generated in the quantum well region 36 that originates in a direction opposite to the p-type contact 40 back out the PhC LED emitter 24.

The configuration of the p-type contact 40 in PhC LEDs is different from that of conventional LEDs. As shown in FIG. 5, a plurality of holes 46 are etched in a surface 48 of the p-type contact 40. The holes 46 terminate above the quantum well region 36 in order for the PhC LED emitter 24 to operate properly. In other words, the holes 46 do not reach the quantum well region 36. Thus, the holes 46 may be referred to as blind holes. The p-type contact 40 with a regular array of holes 46 constitutes the photonic crystal of PhC LEDs. Specifically, the periodic structure of the holes 46 in the p-type contact 40 mimics the way that semiconductor crystals interact with electrons, which only posses energies within certain bands (i.e. ranges of levels of energy) in semiconductor crystals. For example, photonic crystals display unique band structures with zones of allowed wavelengths of light alternating with forbidden wavelength bands. Thus, the photonic structure of PhC LEDs is formed by the contrast in refractive index between filled and empty regions (i.e., holes 46) of the pattern. For example, higher contrast between the filled and empty regions results in increased manipulation of light by the photonic crystal. Thus, photonic crystals may strongly diffract light. As shown in FIG. 5, interaction of the photonic crystal with the confined optical field inside the PhC LED emitter 24 causes the light 32 to diffract and spill out the surface 48, thereby enhancing the brightness of the PhC LED 24. Without the holes 46 in the p-type contact 40, some of the light 32 in conventional LEDs may remain trapped in the p-type contact 40, the n-type contact 38, or the sapphire substrate 42, thereby decreasing the efficiency of the LED.

Figure 6:
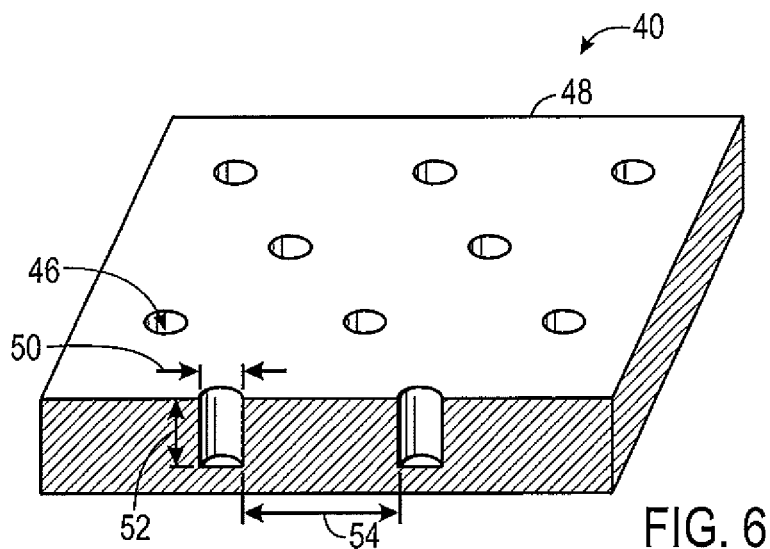
FIG. 6 illustrates a perspective view of a portion of an embodiment of a PhC LED.

The holes 46 of the PhC LED emitter 24 may be arranged in a two-dimensional pattern on the surface 48, as illustrated in the perspective view of the p-type contact 40 shown in FIG. 6. In the illustrated embodiment, the holes 46 have a hexagonal symmetry. In other embodiments, the periodic design of the holes 46 on the surface 48 of the photonic crystal may have a square, triangular, or other type of symmetry. In further embodiments, the photonic crystal may have a quasiperiodic pattern. In addition, the holes 46 have a diameter 50, which may be between approximately 100 nm to 1,000 nm, 200 nm to 800 nm, or 400 nm to 600 nm in certain embodiments. For example, when the p-type contact 40 is configured to operate in the blue-green region of the spectrum, the diameter 50 may be approximately 200 nm. Furthermore, the holes 46 have a depth 52, which does not exceed the height of the p-type contact 40, as discussed above. In other words, the holes 46 do not penetrate through the p-type contact 40. Holes 46 with longer depths 52 may generate stronger photonic crystal action, but may also have an adverse affect on the electrical and optical properties of the diode itself. In addition, holes 46 with relatively straight sidewalls and high depth 52 to diameter 50 ratios (e.g., greater than approximately 3:1) may provide for increased light extraction efficiency. In various embodiments, the depth 52 may be between approximately 100 nm to 1,000 nm, 200 nm to 800 nm, or 400 nm to 600 nm. For example, in one embodiment, the depth is approximately 200 nm. The holes 46 are separated from one another by a separation distance 54, which may be between approximately 100 nm to 1,000 nm, 200 nm to 800 nm, or 400 nm to 600 nm in various embodiments. In one embodiment, the separation distance 54 is approximately 300 nm.

Although shown with circular cross-sections in FIG. 6, in other embodiments, the holes 46 may have other cross-sectional shapes, such as, but not limited to, squares, rectangles, triangles, ovals, and so forth. For example, the cross-sectional shape of the holes 46 may be selected based on the particular fabrication method used to etch the holes 46 in the p-type contact 40. For example, several methods may be used to fabricate photonic crystals, such as, but not limited to, electron beam lithography, holographic lithography, contact-based lithography, nano-imprint lithography, and so forth. Some of these methods may be more suited for certain cross-sectional shapes. The particular configuration of the p-type contact 40, such as the shape, pattern, diameter 50, depth 52, and separation distance 54 of the holes 46, may be selected to increase the amount of light emitted from the PhC LED emitter 24 at the desired wavelength used by the sensor 12.

Figure 7:
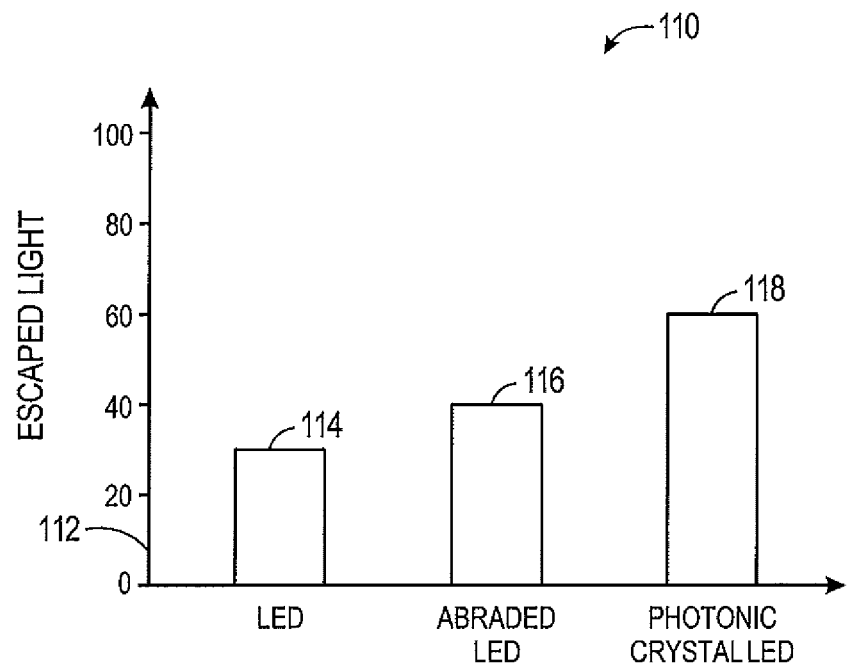
FIG. 7 illustrates a chart comparing escaped light from an embodiment of a PhC LED with that of other LEDs.

The performance characteristics of PhC LEDs may be compared to conventional LEDs using a variety of parameters. For example, FIG. 7 shows a chart 110 comparing escaped light from a PhC LED, such as the PhC LED emitter 24, with that of conventional LEDs. A y-axis 112 represents a percentage of light able to escape the LED. As described in detail above, some of the light produced by conventional LEDs remains trapped within the conventional LED. For example, an amount of escaped light from a conventional LED 114 may be approximately 30 percent. In other words, approximately, 70 percent of the light generated by conventional LEDs may remain trapped within the conventional LED. In an effort to increase the amount of escaped light from LEDs, some conventional LEDs have abraded surfaces. Accordingly, an amount of escaped light from an abraded LED 116 may be approximately 40 percent. Thus, the amount of escaped light is greater in abraded LEDs, but a majority of the light generated in abraded LEDs remains trapped within the abraded LED. The strong diffraction of light enabled by the regular pattern of holes 46 present in PhC LEDs results in an amount of escaped light from a PhC LED 118 of approximately 60 percent. Thus, more than half of the light generated in PhC LEDs may escape from the PhC LED. As improvements in PhC LED technology continues, the amount of escaped light from PhC LEDs 118 may be expected to continue to increase. Less power may be used by PhC LEDs to generate the same amount of light compared with conventional or abraded LEDs because of the increased amount of escaped light from PhC LEDs. Thus, sensors 12 incorporating PhC LEDs may have reduced power consumption rates than sensors using conventional LEDs.

Figure 8:
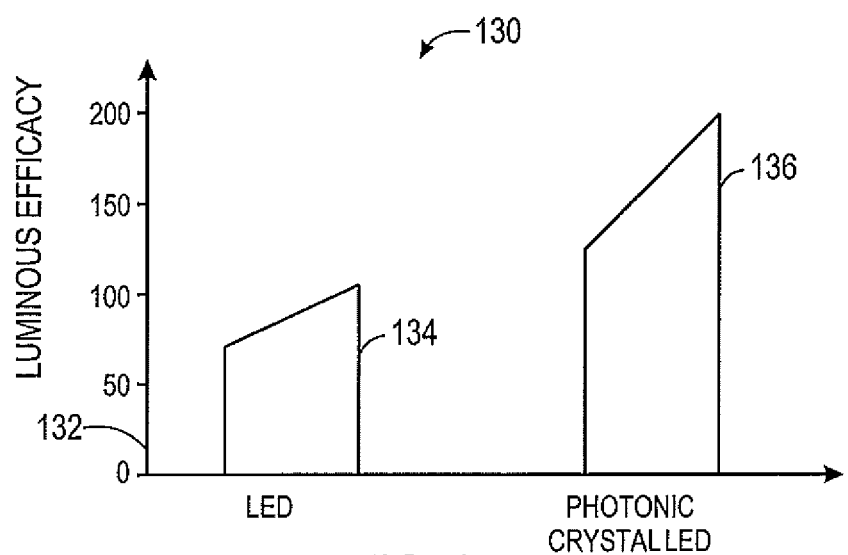
FIG. 8 illustrates a chart comparing luminous efficacy of an embodiment of a PhC LED with that of other LEDs.

Another parameter that may be used to compare PhC LEDs with that of conventional LEDs is luminous efficacy, as illustrated in FIG. 8, which shows a chart 130 of luminous efficacy values. The y-axis 132 represents luminous efficacy, which is a performance characteristic for light sources and is defined as a ratio of luminous flux to power. Luminous flux is defined as a measure of the perceived power of light and may be measured in units of lumens. The units of luminous efficacy used in FIG. 8 are lumens per watt (lm/W). A range of luminous efficacy values for conventional LEDs 134 may be between approximately 75 lm/W to 100 lm/W. A range of luminous efficacy values for PhC LEDs 136 may be between approximately 125 lm/W to 200 lm/W. Thus, the luminous efficacy of PhC LEDs may be greater than that of conventional LEDs. In other words, for the same amount of power, PhC LEDs generate more luminous flux than that of conventional LEDs. Thus, sensors 12 configured to use PhC LEDs, such as PhC emitters 24 and 26 may be configured to use less power than sensors configured to use conventional LEDs. For example, the power supplies for sensors 12 may be smaller than power supplies for sensors using conventional LEDs. Furthermore, sensors 12 using PhC LEDs may generate less heat than conventional sensors because of the lower power consumption rates enabled by PhC LEDs. Accordingly, less heat may be transferred to the patient when using sensors 12 with PhC LEDs.

Figure 9:
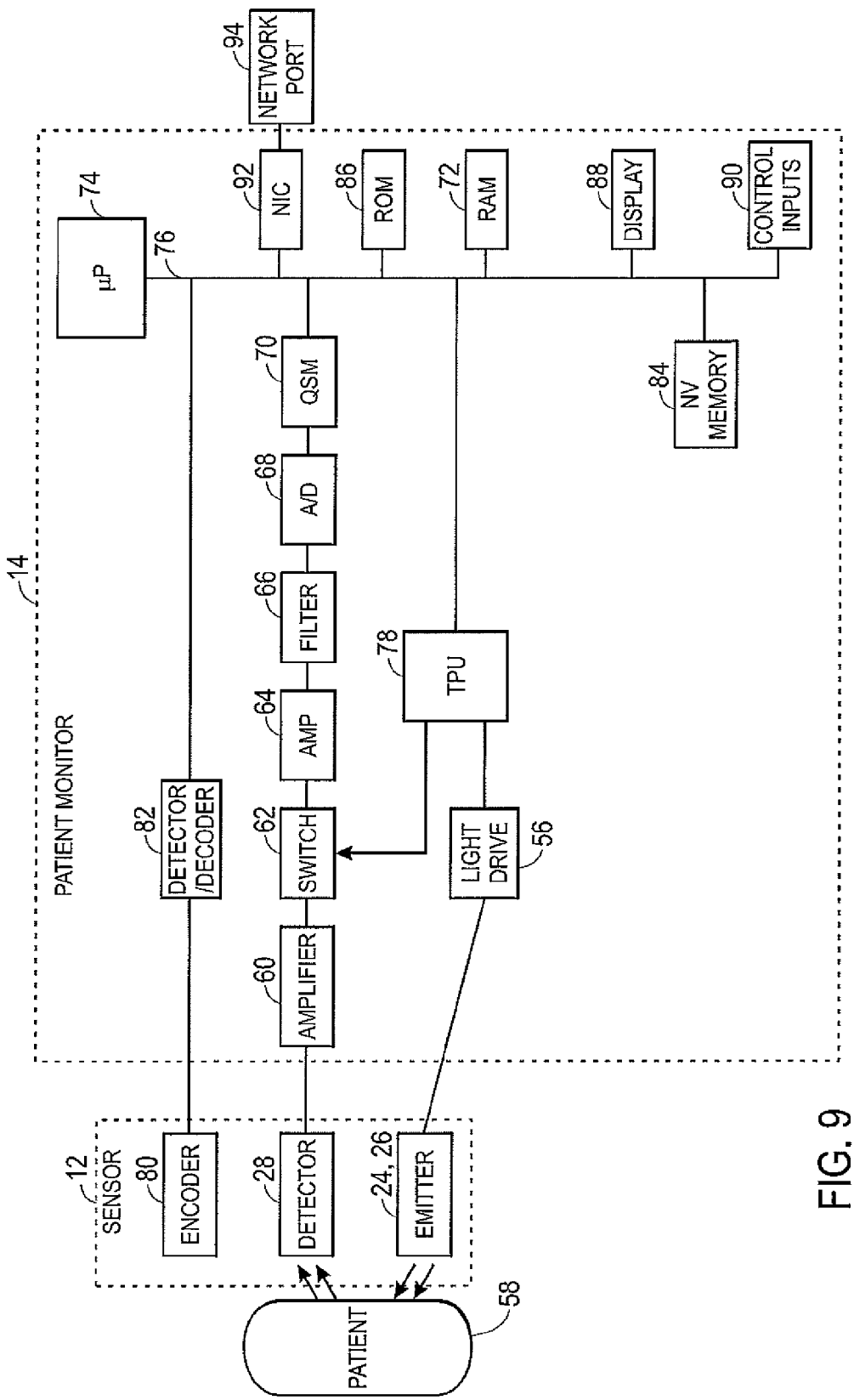
FIG. 9 illustrates a block diagram of an embodiment of a spectrophotometric system.

To illustrate how sensors 12 with PhC LEDs may be configured differently to take advantage of the benefits of PhC LEDs, FIG. 9 depicts a block diagram of an embodiment of a pulse oximeter that may include PhC LEDs. In the illustrated embodiment, a light drive circuitry 56 may drive the emitters 24 and 26. A specific aspect of the light drive circuitry 56 when used with PhC LEDs is discussed in detail below. Light from emitters 24 and 26 passes into a patient's blood perfused tissue 58 and is detected by the detector 28. The detected light may be converted into detector signals, which may be proportional to an intensity of the detected light. The detector signals may then be passed through an amplifier 60, a switch 62, a post-switch amplifier 64, a low band filter 66, and an analog-to-digital converter 68. The digital data may then be stored in a queued serial module (QSM) 70 for later downloading to RAM 72 as the QSM 70 fills up.

In certain embodiments, based at least in part upon the value of the received signals corresponding to the light detected by the detector 28, a microprocessor 74 may obtain the operation status of the emitters 24 and 26. That is, the microprocessor 74 may determine if either of the emitters 24 or 26 has become inoperable or faulty by analyzing the detected light. In other examples, the microprocessor 74 may receive certain signals from the sensor 12 indicative of emitter malfunction. For example, if the emitters 24 or 26 are PhC LED emitters, certain circuitry in the sensor 12 (or in the monitor 14) may measure resistance for each PhC LED and detect a short circuit or other resistance change in the PhC LED or PhC LED circuit. Any suitable circuitry may be used, such as a resistive divider circuitry, suitable for measuring the resistance values of the emitters 24 and 26. Signals representative of emitter malfunctions may then be sent, for example, through an encoder 80 and used in determining the set of operable emitters.

In one embodiment, also connected to a bus 76 may be a time processing unit (TPU) 78 that may provide timing control signals to the light drive circuitry 56. The sensor 12 may also use the encoder 80 for encryption coding that prevents a disposable part of the sensor 12 from being recognized by a detector/decoder 82 that is not able to decode the encryption. In some embodiments, the encoder 80 and/or the detector/decoder 82 may not be present. Additionally or alternatively, the processor 74 may encode and/or decode processed sensor data before transmission of the data to the patient monitor 14.

Nonvolatile memory 84 may store caregiver preferences, patient information, or various parameters. Software for performing the configuration of the monitor 14 and for carrying out the techniques described herein may also be stored on the nonvolatile memory 84, or may be stored on ROM 86. The visual notifications of the operational status of the sensor 12, as well as other may be displayed by display 88 and manipulated through control inputs 90. A network interface card (NIC) 92 may be connected to a network port 94 and used to deliver, for example, the operational status of the sensor 12, any alerts or notifications, and physiologic measurements.

Figure 10:
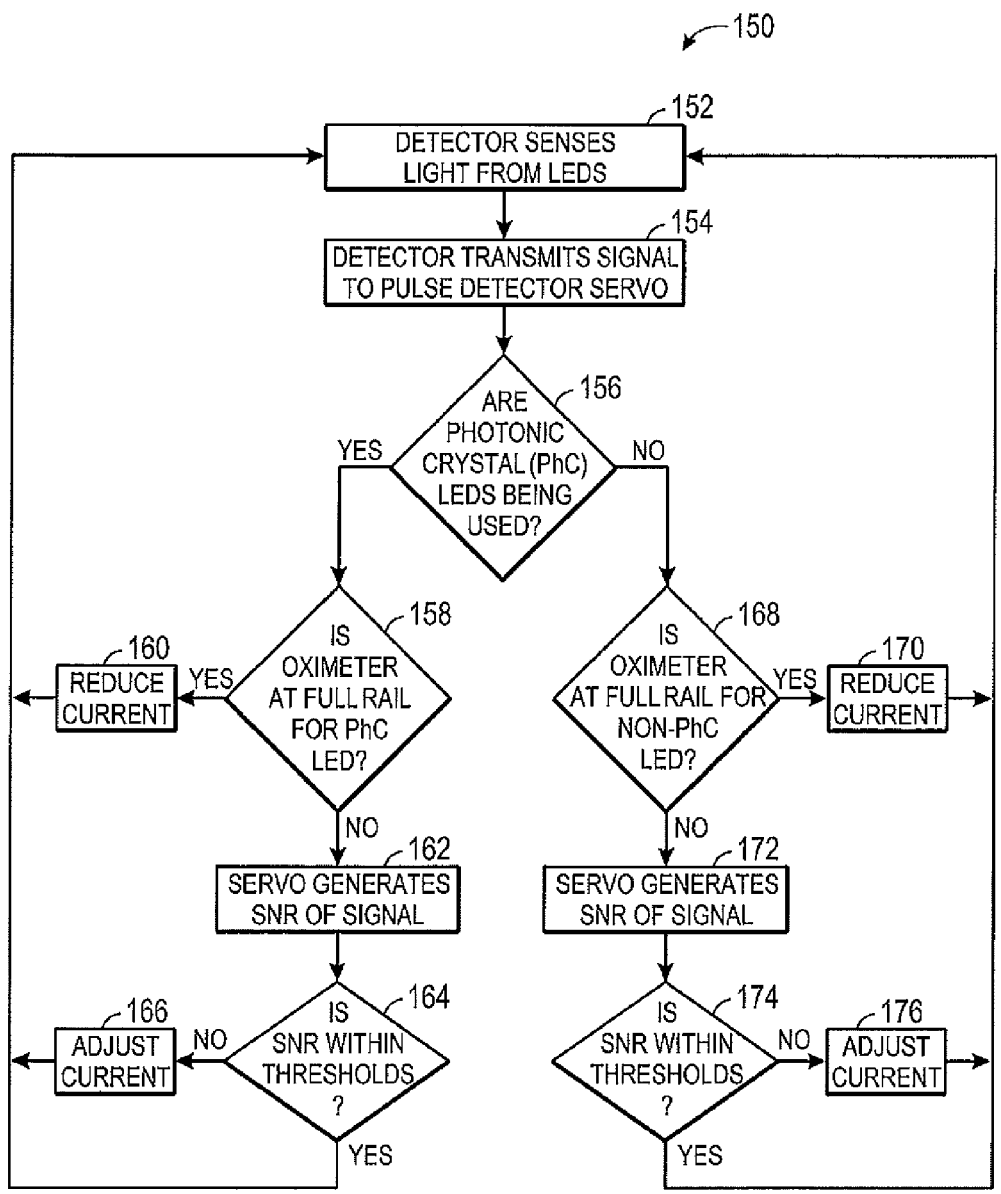
FIG. 10 illustrates a flow chart of a process performed by an embodiment of a pulse detection servo of a spectrophotometric system.

As discussed above, embodiments of the spectrophotometric system 10 that include PhC LEDs may be configured differently because of the lower power consumption rates possible with PhC LEDs. For example, the light drive circuitry 56 of the monitor 14 may include a process suitable for use with PhC LEDs. FIG. 10 shows a flow chart of a process 150 that may be performed by a pulse detection servo, which may reside in the light drive circuitry 56 of an embodiment of the spectrophotometric system 10, such as a pulse oximeter. The pulse detection servo adjusts the current to the emitters 24 and 26 in response to various measured parameters. For example, the process 150 begins with the detector 28 sensing light from the emitters 24 and 26 (block 152). As described in detail above, the emitters 24 and 26 include PhC LEDs. However, in certain embodiments, the sensor 12 may also include conventional LEDs. Next, the detector 28 transmits a signal to the pulse detector servo residing within the light drive circuitry 56 (block 154). The pulse detector servo may then determine whether PhC LEDs are being used by sensor 12 (block 156). For example, the signal from the detector 28 may include information regarding whether the sensor 12 is using PhC LEDs or conventional LEDs. In other embodiments, the sensor 12 may send a separate signal to the pulse detector servo indicating whether the PhC LEDs are being used.

If PhC LEDs are being used, the pulse detector servo then determines whether the oximeter is at full rail for the PhC LEDs (block 158). For example, the oximeter is at full rail when excess current has been driven through the LEDs of the oximeter. If the pulse detector servo determines that the oximeter is at full rail, the current through the PhC LED is reduced (block 160). The process 150 then returns to sensing light from the emitters 24 and 26 using the detector 28 (block 152). If the oximeter is not a full rail for the PhC LEDs, the servo generates a signal-to-noise ratio (SNR) of the signal from the detector 28 (block 162). The signal generated by the detector 28 typically contains components of noise introduced by the electronics of the oximeter, by the patient, and by the environment. Noisy signals have a low SNR. The pulse oximeter may not be able to identify the blood oxygen saturation accurately when the SNR of the signal is below a lower threshold. Increasing the current through the LEDs of the sensor 12 causes the LEDs to generate more light. The SNR of the signal is higher because the detector 28 is able to sense more of the light from the LEDs. However, increasing the current to the LEDs to improve the SNR causes the sensor 12 to consume more power and generate more heat. Thus, an upper threshold may be established for the SNR that provides an acceptable SNR and yet reduces the power consumption of the sensor 12. As discussed in detail above, PhC LEDs may generate more light using less current than conventional LEDs. Thus, for the same SNR thresholds, use of PhC LEDs enables the sensor 12 to use less current, consume less power, and generate less heat. Alternatively, the upper threshold of the SNR for PhC LEDs may be increased compared to that of conventional LEDs. Thus, for the same power consumption level, the signals provided by PhC LEDs may be better than those provided by conventional LEDs. In other words, the upper and lower thresholds may be selected based at least in part on various performance characteristics of PhC LEDs, such as, but not limited to, percentage of escaped light and luminous efficacy. In addition, reduced heat generation may improve patient comfort and/or enable the sensor 12 to be placed on a patient for longer periods of time. If the SNR is not within the established thresholds, the servo adjusts the current to the PhC LEDs as needed (block 166) and returns to block 152. If the SNR is within the thresholds, the process 150 returns to block 152.

If the PhC LEDs are not being used, the process 150 determines whether the oximeter is at full rail for the conventional LEDs (block 168). The full rail condition for the conventional LEDs may be different from the full rail condition for the PhC LEDs. For example, the full rail condition for the PhC LEDs may be greater than that of the conventional LEDs because of the greater efficiency of the PhC LEDs. If the servo determines that the oximeter is at full rail, the current through the conventional LEDs is reduced (block 170) and the process 150 returns to block 152. If the oximeter is not at full rail, the servo generates the SNR of the signal (block 172). Next, the servo determines whether the SNR is within the lower and upper thresholds (block 174). As discussed above, the thresholds of the SNR using conventional LEDs may be different from the thresholds of the SNR using PhC LEDs. If the SNR is not within the thresholds, the process 150 adjusts the current appropriately (block 176) and returns to block 152. Because of the lower efficiency of conventional LEDs, more current may be necessary to achieve the same SNR as with PhC LEDs. Thus, sensors 12 using conventional LEDs may use more current, consume more power, and generate more heat to achieve the same SNR as sensors 12 using PhC LEDs. If the SNR is within the threshold, the process 150 returns to block 152.

While the disclosure may be susceptible to various modifications and alternative forms, specific embodiments have been shown by way of example in the drawings and have been described in detail herein. However, it should be understood that the embodiments provided herein are not intended to be limited to the particular forms disclosed. Rather, the various embodiments may cover all modifications, equivalents, and alternatives falling within the spirit and scope of the disclosure as defined by the following appended claims.

What is claimed is:

1. A system comprising:
   a spectrophotometric sensor configured to be operatively coupled to the monitor, the spectrophotometric sensor comprising:
   one or more emitters configured to transmit light into tissue, wherein the light has a wavelength adapted to obtain a physiologic measurement, and wherein the one or more emitters comprise a photonic crystal light emitting diode (LED) or a conventional LED; and a detector configured to receive the light from the tissue and output a signal proportional to an intensity of the light from the tissue; and a monitor comprising a drive interface configured to:

determine whether the one or more emitters transmitting light into the tissue comprise a photonic crystal LED or a conventional LED;

determine whether an excess current is being driven through the one or more emitters; and adjust a current driving the one or more emitters to a first level if the one or more emitters comprise the photonic crystal LED or to a second level if the one or more emitters comprise the conventional LED, wherein adjusting the current driving the one or more emitters is based at least in part on whether excess current is being driven through the one or more emitters and on a signal-to-noise ratio of the signal generated by the detector.

2. The system of claim 1, wherein the photonic crystal LED comprises a p-type contact, a quantum well region, and an n-type contact.

3. The system of claim 2, wherein an external surface of the p-type contact comprises a plurality of blind holes, wherein each of the plurality of blind holes has a depth less than a thickness of the p-type contact.

4. The system of claim 3, wherein the plurality of blind holes are arranged in a regular pattern.

5. The system of claim 1, wherein a percentage of escaped light from the photonic crystal LED is greater than approximately 60 percent.

6. The system of claim 1, wherein a luminous efficacy of the photonic crystal LED is greater than approximately 125 lumens per watt.

7. The system of claim 1, wherein the light is at least partially collimated.

8. The system of claim 1, wherein the spectrophotometric sensor is configured for a reflectance mode of operation or a transmittance mode of operation.

9. The system of claim 1, wherein the physiologic measurement is a pulse oximetry measurement.

10. The system of claim 1, wherein the monitor comprises a pulse oximetry monitor.

11. The system of claim 1, wherein the drive interface is configured to decrease the drive current if the signal-to-noise ratio of the signal output from the detector is greater than an upper threshold, and to increase the drive current if the signal-to-noise ratio of the signal output from the detector is less than a lower threshold.

12. The system of claim 11, wherein a luminous efficacy of the photonic crystal LED is greater than approximately 125 lumens per watt.

13. The system of claim 12, wherein the upper and lower thresholds are selected based at least in part on the luminous efficacy of the photonic crystal LED.

14. A method comprising:

emitting a wavelength of light from an emitter into a patient, wherein the light is generated by a photonic crystal light emitting diode (LED) or a conventional LED;

detecting the light from the patient and generating a signal proportional to an intensity of the light using a detector;

determining if the emitter generating the wavelength of light is the photonic crystal LED or the conventional LED;

determining whether an excess current is being driven through the emitter; and adjusting a current driving the emitter to a first level if the emitter is the photonic crystal LED or to a second level if the emitter is the conventional LED, wherein adjusting the current driving the emitter is based at least in part on whether excess current is being driven through the emitter and on a signal-to-noise ratio of the signal generated by the detector.

15. The method of claim 14, comprising comparing a threshold and the signal-to-noise ratio of the signal generated by the detector using a monitor operatively coupled to the emitter and the detector.

16. The method of claim 15, comprising adjusting the current driving the emitter if the signal-to-noise ratio of the signal generated by the detector is greater than an upper threshold, and adjusting the current driving the emitter if the signal-to-noise ratio of the signal generated by the detector is less than a lower threshold.

17. The method of claim 16, comprising selecting the upper and lower thresholds based at least in part on a performance characteristic of the photonic crystal LED.

18. The method of claim 16, comprising decreasing the current driving the emitter if the signal-to-noise ratio of the signal generated by the detector is greater than the upper threshold.

19. The method of claim 16, comprising increasing the current driving the emitter is the signal-to-noise ratio of the signal generated by the detector is less than the lower threshold.

20. The method of claim 14, wherein the light is scattered from a tissue of the patient or the light is transmitted through the tissue of the patient.

21. A monitor comprising:

one or more spectrophotometric sensor inputs configured to receive a signal from a spectrophotometric sensor, wherein the spectrophotometric sensor comprises:

one or more emitters configured to transmit light into tissue, wherein the light has a wavelength configured to obtain a physiologic measurement, and wherein the one or more emitters comprises a photonic crystal light emitting diode (LED) or a conventional LED; and a detector configured to receive the light from the tissue and output the signal to the one or more spectrophotometric sensor inputs, wherein the signal is proportional to an intensity of the light from the tissue; and a drive interface configured to:

determine whether the one or more emitters transmitting light into the tissue comprise a photonic crystal LED or a conventional LED;

determine whether an excess current is being driven through the one or more emitters; and adjust a current driving the one or more emitters to a first level if the one or more emitters comprise the photonic crystal LED or to a second level if the one or more emitters comprise the conventional LED, wherein adjusting the current driving the one or more emitters is based at least in part on whether excess current is being driven through the one or more emitters and on a signal-to-noise ratio of the signal generated by the detector.

* * * * *